(12) United States Patent
Flynn et al.

(10) Patent No.: US 8,828,036 B2
(45) Date of Patent: Sep. 9, 2014

(54) SURGICAL CUTTING INSTRUMENT WITH SUCTION PASSAGE FORMING MEMBER DISPOSED OVER OUTER TUBULAR BODY

(71) Applicant: Gyrus ENT L.L.C., Bartlett, TN (US)

(72) Inventors: John P. Flynn, Collierville, TN (US); Kevin C. Edwards, Olive Branch, MS (US)

(73) Assignee: Gyrus Ent, L.L.C., Bartlett, TN (US)

( * ) Notice: Subject to any disclaimer, the term of this patent is extended or adjusted under 35 U.S.C. 154(b) by 89 days.

(21) Appl. No.: 13/742,822

(22) Filed: Jan. 16, 2013

(65) Prior Publication Data
US 2013/0131706 A1 May 23, 2013

Related U.S. Application Data

(63) Continuation of application No. 13/013,117, filed on Jan. 25, 2011, now Pat. No. 8,377,086.

(51) Int. Cl.
| | |
|---|---|
| *A61B 17/32* | (2006.01) |
| *A61B 10/02* | (2006.01) |
| *A61B 17/16* | (2006.01) |
| A61B 17/00 | (2006.01) |

(52) U.S. Cl.
CPC .......... *A61B 17/32* (2013.01); *A61B 17/32002* (2013.01); *A61B 10/0283* (2013.01); *A61B 2017/320024* (2013.01); *A61B 17/1644* (2013.01); *A61B 2017/00353* (2013.01); *A61B 2217/005* (2013.01); *A61B 10/0275* (2013.01); *A61B 2017/00973* (2013.01)
USPC ......................................................... 606/170

(58) Field of Classification Search
USPC ........... 606/76, 80, 83, 169, 170–180; 604/22
See application file for complete search history.

(56) References Cited

U.S. PATENT DOCUMENTS

| | | |
|---|---|---|
| 3,882,872 A | 5/1975 | Douvas et al. |
| 3,937,222 A | 2/1976 | Banko |
| 4,844,064 A | 7/1989 | Thimsen et al. |

(Continued)

FOREIGN PATENT DOCUMENTS

EP      0 558 846 A1    9/1993

OTHER PUBLICATIONS

Apr. 12, 2012 International Search Report and Written Opinion issued in Application No. PCT/US2012/020176.
Jul. 13, 2012 Quayle Action issued in U.S. Appl. No. 13/013,117.

(Continued)

*Primary Examiner* — Tuan V Nguyen
(74) *Attorney, Agent, or Firm* — Oliff PLC (57) ABSTRACT

A surgical instrument having a first cutting blade and a second cutting blade that rotates within the first cutting blade during a cutting operation to cause cutting windows of the cutting blades to remove tissue from a patient also includes a suction passage forming member disposed over a suction aperture of the first cutting blade. The suction passage forming member includes an inlet, an outlet and a passage between the inlet and the outlet, the outlet communicating with the suction aperture. The surgical instrument can be used as a suction tool by applying a vacuum through an internal bore of the second cutting blade while the second cutting blade is stopped from rotating with the cutting windows of the first and second cutting blades misaligned with each other so that the vacuum is applied through the suction aperture and the suction passage forming member.

19 Claims, 6 Drawing Sheets

(56) References Cited

U.S. PATENT DOCUMENTS

| | | |
|---|---|---|
| 5,674,235 A | 10/1997 | Parisi |
| 5,730,752 A | 3/1998 | Alden et al. |
| 5,730,754 A | 3/1998 | Obenchain |
| 5,779,662 A | 7/1998 | Berman |
| 6,342,061 B1 | 1/2002 | Kauker et al. |
| 6,423,078 B1 | 7/2002 | Bays et al. |
| 6,979,332 B2 * | 12/2005 | Adams ............................ 606/45 |
| 7,247,161 B2 | 7/2007 | Johnston et al. |
| 7,318,831 B2 | 1/2008 | Alvarez et al. |
| 8,377,086 B2 | 2/2013 | Flynn et al. |
| 2003/0163126 A1 | 8/2003 | West, Jr. |
| 2012/0191117 A1 | 7/2012 | Palmer et al. |
| 2012/0215245 A1 | 8/2012 | Palmer et al. |

OTHER PUBLICATIONS

Dec. 12, 2012 Notice of Allowance issued in U.S. Appl. No. 13/013,117.

* cited by examiner

SURGICAL CUTTING INSTRUMENT WITH SUCTION PASSAGE FORMING MEMBER DISPOSED OVER OUTER TUBULAR BODY

This is a continuation of U.S. patent application Ser. No. 13/013,117 filed Jan. 25, 2011 (now U.S. Pat. No. 8,377,086), the disclosure of which is incorporated herein by reference in its entirety.

BACKGROUND

This disclosure relates to surgical instruments, and in particular to surgical cutting instruments that use suction, for example, powered shavers, microdebriders and dissector blades.

Surgical apparatus used to shave, cut, resect, abrade and/or remove tissue, bone and/or other bodily materials are known. Such surgical apparatus can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (located at a side of the distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held in place by the powered handpiece.

In some instruments the inner tube is hollow and has a cutting window on a side surface of its distal end such that tissue, bone, etc. will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc. as the inner tube is rotated within the outer tube.

In some instruments a vacuum is applied through the inner tube such that the bodily material that is to be cut, shaved, etc. is drawn into the windows of the inner and outer tubes when those windows become aligned, thereby facilitating the cutting, shaving, etc. of the tissue, which then travels through the inner tube due to the suction. It also is common to supply an irrigation fluid, which can include a liquid, to the surgical site via a passage provided between the inner and outer tubes.

SUMMARY

Many times during surgery, the surgeon wishes to apply suction to the surgical site without performing cutting with the surgical instrument. This usually is done by withdrawing the surgical instrument and inserting a dedicated suction device (for example, a suction wand which is a tube to which suction is applied). However, exchanging the surgical tool for the dedicated suction device is time-consuming. Furthermore, insertion and removal of instruments into the patient can cause trauma and irritation to the passage of the patient, and thus it is desirable to minimize the number of times that surgical instruments need to be withdrawn and inserted/reinserted into the patient.

It is conceivable that the surgeon can use the surgical cutting instrument as a suction device, for example, by stopping rotation of the inner cutting tube while continuing to apply suction through the inner tube. By careful operation of the pedal (or other control device) which controls the rotation of the inner tube, the surgeon can cause the cutting windows of the inner and outer tubes to be aligned with each other such that suction can be applied to the surgical site through the aligned windows of the inner and outer tubes. However, because the windows of the inner and outer tubes are cutting surfaces (and typically include serrations), most surgeons choose not to use the surgical cutting tool as a suctioning device because tissue adjacent to the outer tube window tends to be drawn into the window and partially cut and/or irritated by the cutting surfaces of the inner and outer tubes. Additionally, because the cutting windows of the inner and outer tubes are disposed on a side surface of the distal tips of the inner and outer tubes, the suction is applied from the side of the distal end of the tube, which is not optimal. Most suction wands apply the suction from the very end of the tip such that suction is applied at the very tip of the suction wand.

According to an aspect of the invention, a surgical instrument that performs cutting also can function as a suction wand. This is achieved by providing a surgical instrument having a first cutting blade and a second cutting blade that rotates within the first cutting blade during a cutting operation to cause cutting windows of the cutting blades to remove tissue from a patient, and by including a suction aperture disposed at a side of the first cutting blade near the distal end of the first cutting blade and opposite to the side containing the cutting window, and by providing a suction passage forming member disposed over the suction aperture of the first cutting blade. The suction passage forming member includes an inlet, an outlet and a passage between the inlet and the outlet, the outlet communicating with the suction passage, and the inlet facing distally. The surgical instrument can be used as a suction tool by applying a vacuum through an internal bore of the second cutting blade while the second cutting blade is stopped from rotating such that the cutting windows of the first and second cutting blades are misaligned with each other and so that the vacuum is applied through the suction aperture and the suction passage forming member.

In accordance with some embodiments, the suction aperture provided in the first cutting blade is an elongated slot. The elongated slot is substantially smaller than the cutting window of the first cutting blade. When the surgical instrument is used for cutting, most of the suction is applied through the cutting windows because the cutting windows are substantially larger than the suction aperture. In addition, when the cutting windows are aligned with each other (such that tissue to be cut will be drawn into the windows), the suction aperture is blocked by the second (inner) cutting blade.

The suction passage forming member has a distal end at which the inlet of the suction passage forming member is located. According to some embodiments, the distal end of the suction passage forming member is tapered to ease insertion of the surgical instrument into a passage of a patient. This compensates for the increase in diameter of the surgical instrument that is caused by the suction passage forming member.

In accordance with some embodiments, the suction passage forming member is a half tube that is attached to an outer surface of the first cutting blade so as to cover the suction aperture. The half tube includes a closed end and an open end, the open end defining the inlet of the suction passage forming member. The open end preferably is tapered to ease insertion of the surgical instrument into a passage of a patient. Preferably, the half tube is made from the same material used to make the first cutting blade. For example, if the first cutting blade is metallic, then preferably the half tube also is metallic, and can be welded to the first cutting blade during manufacture of the surgical instrument.

According to another embodiment, the suction passage forming member is a tube that fits over the distal end of the first cutting blade. The tube includes a radially protruding portion in which the passage of the suction passage forming member is disposed. The part of the tube forming the inlet of the suction passage forming member preferably is tapered to ease insertion of the surgical instrument into the patient passage. The tube can be metallic or plastic, and preferably is slidably detachable and attachable to the first cutting blade.

In accordance with preferred embodiments, the surgical instrument also includes a passage between the first and second cutting blades through which a liquid can be supplied.

A surgical method that uses the surgical instrument includes a step of inserting the surgical instrument into a passage of a patient, and then performing a suctioning operation. The suctioning operation includes positioning the second cutting blade relative to the first cutting blade so that the cutting windows of the first and second cutting blades are misaligned with each other so that the internal bore of the second cutting blade does not communicate with the passage of the patient through either of the cutting windows of the first and second cutting blades. While positioning the windows of the cutting blade as described above, a vacuum is applied through the internal bore of the second cutting blade to draw material from the passage of the patient into the internal bore of the second cutting blade through the suction passage forming member and the suction aperture. During the suction operation, the first and second cutting blades are not rotated relative to each other.

The second cutting blade can be positioned relative to the first cutting blade so that the cutting windows of the first and second cutting blades are misaligned with each other by the surgeon operating the controls of the surgical instrument (for example, by operating a foot pedal) while observing the distal tip of the cutting instrument (for example, with an endoscope as is typically used to observe the surgical procedure) until the cutting window of the inner, second cutting blade is misaligned with the cutting window of the outer, first cutting blade such that the back side of the second cutting blade opposite to the window substantially blocks the window of the first cutting blade.

Furthermore, a cutting operation can be performed either before, after, or both before and after, performing the suction operation. The cutting operation includes rotating the second cutting blade relative to the first cutting blade while applying the vacuum through the internal bore of the second cutting blade. Furthermore, a liquid can be supplied through a passage that exists between the first and second cutting blades during the cutting operation.

Whether the suctioning operation is performed before, after, or both before and after a cutting operation, it is unnecessary to withdraw the cutting instrument when switching between a cutting operation and a suctioning operation. Furthermore, a separate suction wand may not be needed.

BRIEF DESCRIPTION OF THE DRAWINGS

Various exemplary embodiments of the disclosed surgical tool will be described in detail with reference to the following drawings in which.

DETAILED DESCRIPTION OF EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 1:
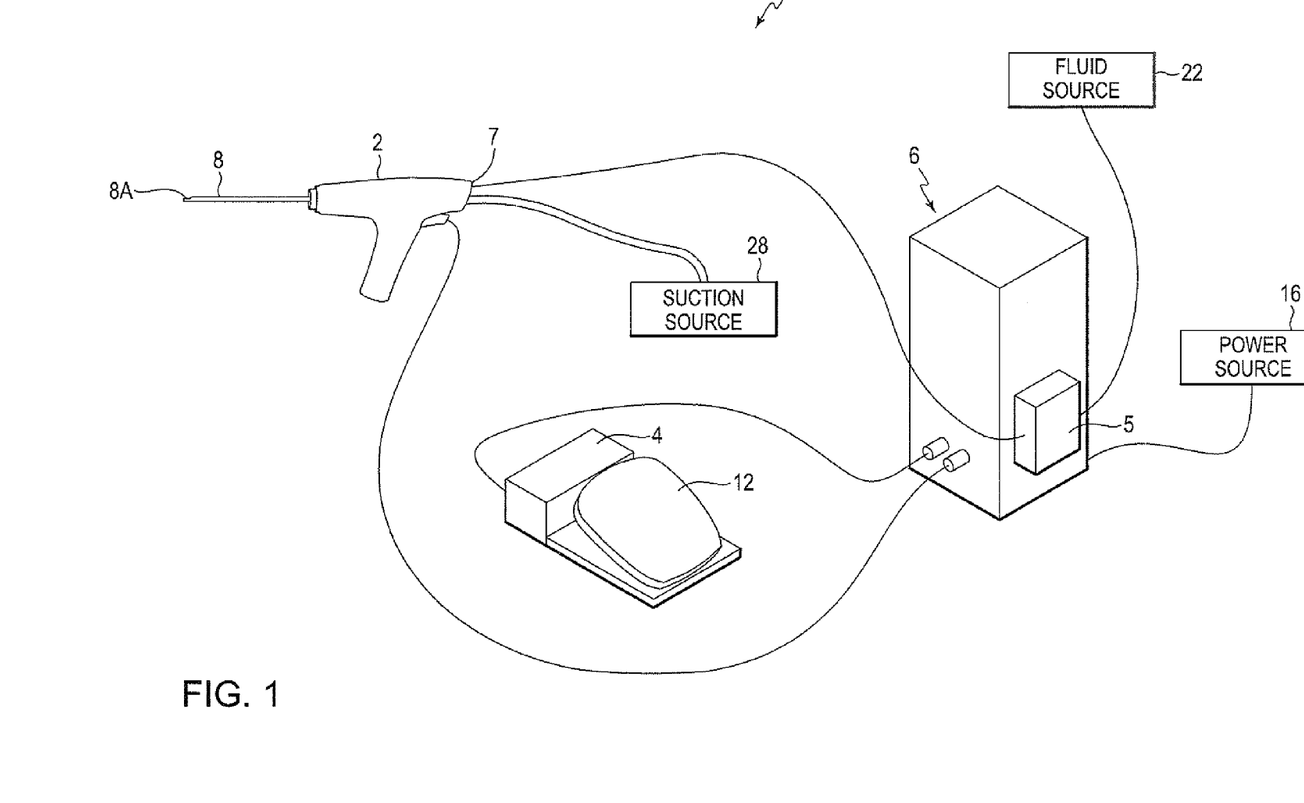
FIG. 1 illustrates a perspective view of a powered surgical tool system that incorporates a surgical instrument, control unit, fluid source and suction source.

FIG. 1 is a schematic of a powered surgical tool system. Except for the tip of the cutting tool, to be described hereafter, the system may be in accordance with the system described in U.S. Pat. No. 7,247,161, the disclosure of which is incorporated herein by reference in its entirety. Another system to which the invention is applicable is described in U.S. Pat. No. 7,318,831, the disclosure of which is incorporated herein by reference in its entirety. As shown in FIG. 1, the powered surgical tool system 1 includes a handle 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet mounted on a wall. The handle 2 is connected, at its distal end, to a surgical instrument 8. The surgical instrument 8 in this embodiment includes a cutting tip at its distal end 8A that is used, for example, to cut, shave, remove, resect and/or abrade tissue, bone and/or other bodily materials.

Figure 2:
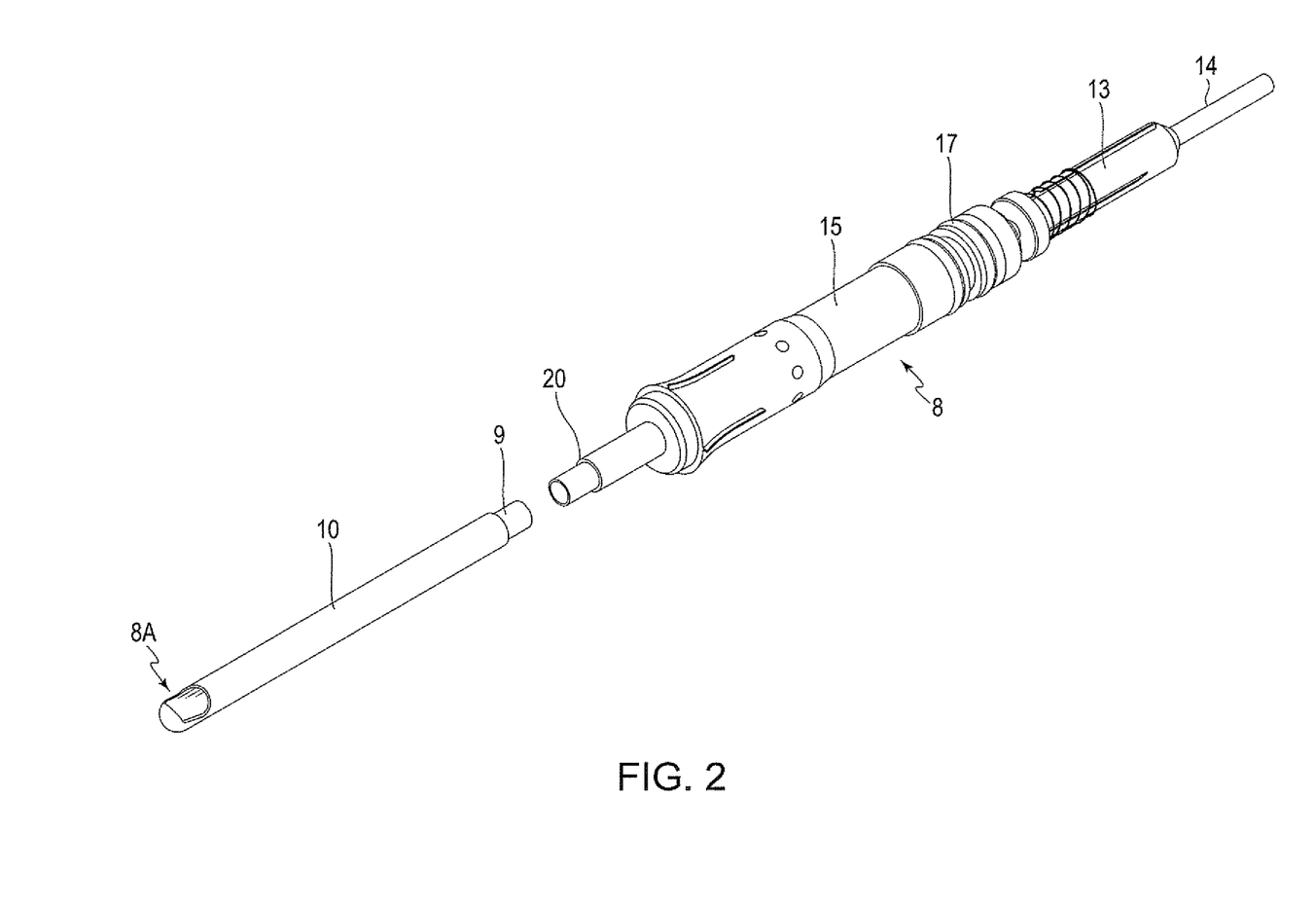
FIG. 2 is a perspective view of an exemplary embodiment of a surgical instrument in accordance with the present disclosure.

FIG. 2 illustrates a perspective view of an exemplary embodiment of the surgical instrument 8 in accordance with aspects of the invention. The instrument 8 incorporates an inner tube 9 and an outer tube 10. In this exemplary embodiment, an inner tube hub 13 is formed on the second end 14 of the inner tube 9 and an outer tube hub 15 is formed on the second end 17 of the outer tube 10. The inner tube 9 is inserted into a fluid passage 20 formed within the outer tube 10 so that the inner tube 9 is co-axially disposed within the outer tube 10 until the external distal tip of inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube.

The inner and outer tube hubs 13, 15 couple the inner and outer tubes 9, 10, respectively, to the handle 2. Once coupled to the handle 2, the outer tube 10 will be fixed relative to the handle 2, but the inner tube 9 will be rotatable relative to the outer tube 10 and the handle 2.

Figure 3:
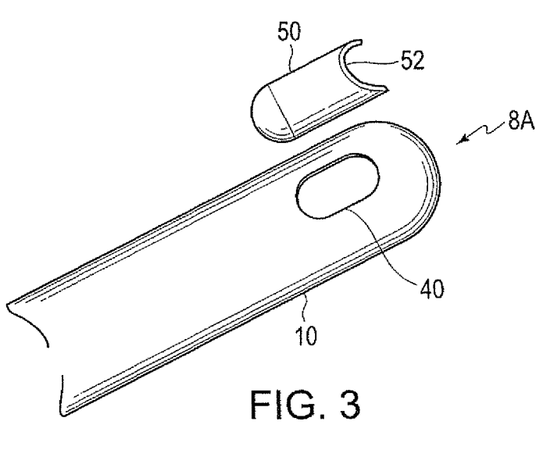
FIG. 3 is an exploded, perspective view of a distal tip of a surgical instrument in accordance with a first embodiment showing the suction passage forming member of one embodiment separated from the outer cutting blade.

FIG. 3 is a perspective view of the distal tip 8A of the surgical instrument 8 according to a first embodiment. As shown in FIG. 3, a suction aperture 40 is provided near the distal end of the outer tube 10. The suction aperture 40 is provided on a side of the distal end of the outer tube 10 opposite to a side containing the cutting window of the outer tube 10 (the cutting window is not shown in FIG. 3). In the FIG. 3 embodiment, the suction passage forming member is a half tube 50. The half tube 50 includes an inlet 52 through which the suction will be applied to the patient passage during a suctioning operation to be described in more detail below.

Figure 4:
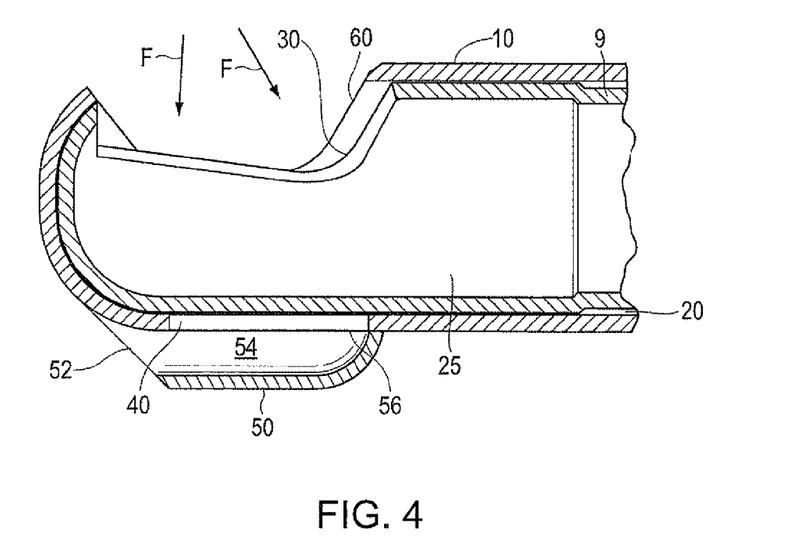
FIG. 4 is a side, cross-sectional view of the FIG. 3 embodiment showing the cutting windows of the inner and outer cutting blades in complete alignment as occurs during a cutting operation.
Figure 5:
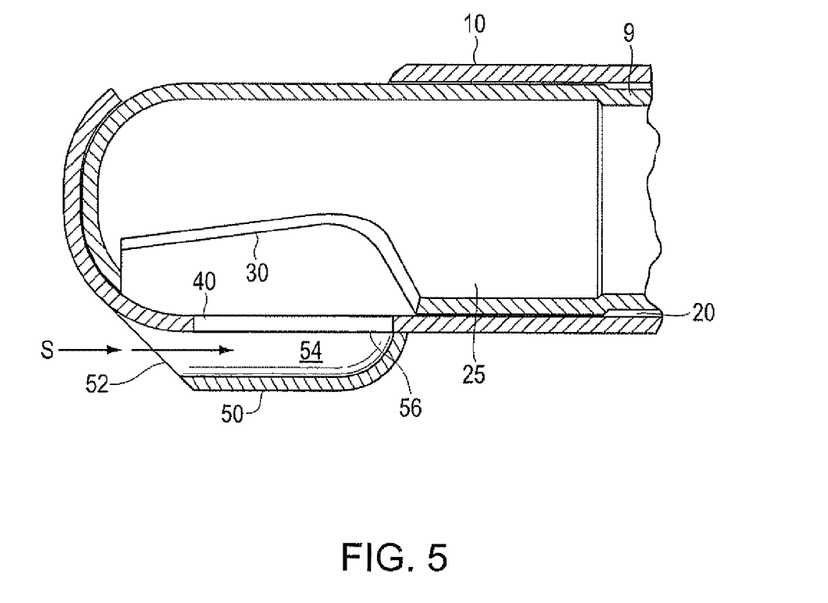
FIG. 5 is a side, cross-sectional view similar to FIG. 4, but with the cutting windows being in complete mis-alignment so that the surgical instrument can used as a suction device.

FIGS. 4 and 5 are side, cross-sectional views of the FIG. 3 embodiment. FIG. 4 shows the positions of the inner tube 9 and the outer tube 10 when the cutting windows of those tubes are in alignment (as occurs during a cutting operation as the inner tube 9 is rotated within the outer tube 10). FIG. 5 shows the positions of the inner tube 9 and the outer tube 10 when the cutting windows of those tubes are in misalignment (as occurs during a suctioning operation).

The outer tube 10 includes a cutting window 60 disposed at a side of its distal end. Thus, the outer tube 10 also can be referred to as a first cutting blade. The inner tube 9 also includes a cutting window 30 disposed at a side of its distal end. Thus, the inner tube 9 also can be referred to as a second cutting blade. The edges of the cutting windows 30 and 60 can be serrated, smooth or a combination of serrated and smooth to form cutting surfaces. As mentioned previously, the inner cutting blade 9 rotates within the outer cutting blade 10, and thus as the inner cutting blade 9 rotates, the cutting windows 30 and 60 become aligned with each other as shown in FIG. 4 and then become misaligned with each other as shown in FIG. 5. When the cutting windows 30 and 60 are misaligned with each other as shown in FIG. 5, the side of the inner tube 9 distal tip opposite from the cutting window 30 blocks the cutting window 60 of the outer cutting blade 10, as will be described in more detail below.

The first, or outer cutting blade 10 thus is a tubular body having a proximal end and a distal end, with the cutting window 60 disposed at a side of the first cutting blade 10 near the distal end.

The inner, second cutting blade 9 is a tubular body having a proximal end and a distal end, with the cutting window 30 disposed at a side of its distal end. As mentioned previously, the second, inner cutting blade 9 is rotabably disposed inside of the first, outer cutting blade 10 such that the surgical instrument 8 cuts tissue by rotating the second, inner cutting blade 9 within the first, outer cutting blade 10 while a vacuum is applied through an internal bore 25 of the cutting blade 9 to draw the tissue into the cutting windows 30 and 60 of the cutting blades 9 and 10 and sever the tissue by rotation of the cutting blade 9.

The first, outer cutting blade 10 includes a suction aperture 40, shown in FIGS. 3-5, at a side of its distal end opposite to the side in which the cutting window 60 is formed. In a preferred embodiment, the suction aperture 40 is an elongated slot having rounded ends. When the inner cutting blade 9 is stopped while in the position shown in FIG. 5 such that the cutting windows 30 and 60 are misaligned, suction applied through the internal bore 25 of the inner cutting blade 9 will be applied through the suction aperture 40 of the outer cutting blade 10. However, because the suction aperture 40 is disposed at a side of the distal end of the outer cutting blade 10, such suction is not optimal if the suction passage forming member (the half tube 50 of the embodiment of FIGS. 3-5) is not provided. In particular, without the suction passage forming member, tissue tends to be drawn into the suction aperture 40 and could be severed or at least irritated by the opening 40. In addition, if suction passage forming member is not provided, tissue would tend to be sucked into the suction aperture 40 during a cutting operation and thus become severed as the inner cutting blade 9 is rotated. Furthermore, the suction that is applied through suction aperture 40 is not directed towards the distal tip of the surgical instrument 8, but instead is directed toward a side at the distal end of the surgical instrument 8.

Accordingly, a suction passage forming member is disposed over the suction aperture 40 of the outer cutting blade 10. The suction passage forming member includes an inlet, an outlet and a passage between the inlet and the outlet. The outlet communicates with the suction aperture 40, whereas the inlet faces distally.

In the embodiment of FIGS. 3-5, the suction passage forming member is a half tube 50. The half tube 50 is attached to the outer surface of the outer cutting blade 10 over the suction aperture 40. The half tube 50 includes an inlet 52, an internal passage 54 and an outlet 56 that communicates with the suction aperture 40. Accordingly, and as shown in FIG. 5, the surgical instrument 8 can be used as a suction tool by applying the vacuum through the internal bore 25 of the cutting blade 9 while the cutting blade 9 is stopped from rotating and the cutting windows 30 and 60 of the cutting blades 9 and 10 are misaligned with each other as shown in FIG. 5. When in the FIG. 5 position, the vacuum applied through the internal bore 25 is applied through a suction passage defined by the suction aperture 40, the outlet 56, the internal passage 54 and the inlet 52 of the half tube 50.

The surgeon operating the instrument 8 can cause the windows 30 and 60 to become oriented in the misaligned state shown in FIG. 5 by, for example, tapping on the pedal 12 that controls the instrument to cause incremental rotation of the inner cutting blade 9 while observing the distal tip of the instrument, for example, by an endoscope, which usually also is disposed at the operating site, until the windows 30 and 60 obtain the state shown in FIG. 5. While the windows 30 and 60 are misaligned as shown in FIG. 5, vacuum can be applied through the internal bore 25 of the cutting blade 9 so that the surgical instrument can be used like a suction wand. The flow of the fluid toward the suction passage defined by the suction aperture 40 and the half tube 50 is illustrated by arrow S in FIG. 5, whereas the flow that occurs during a cutting operation is illustrated by arrows F in FIG. 4.

Although it is not necessary, irrigation fluid also could be supplied through bore 20 when in the state shown in FIG. 5.

When the surgical instrument is used for cutting (that is, when the inner cutting blade 9 is being rotated within the outer cutting blade 10 while irrigation liquid and suction are applied), most of the suction is applied through the cutting windows 30 and 60 because they are much larger than the suction aperture 40 and because the portion of the inner cutting blade 9 distal end other than the cutting window 30 blocks the suction aperture 40 for much of the rotation.

As noted above, the half tube 50 prevents the suction aperture 40 from functioning like a cutting window by preventing tissue from entering into the suction aperture 40.

The half tube 50 can be attached to the outer cutting blade 10 during the manufacturing process of the outer cutting blade 10. For example, when the outer cutting blade 10 is made from a metal material, the half tube 50 also can be made from the same metal material and welded to the cutting blade 10.

The cutting blades 9 and 10 are made from a sterilizable material. According to some embodiments, the sterilizable material is a metal such as stainless steel.

Figure 6:
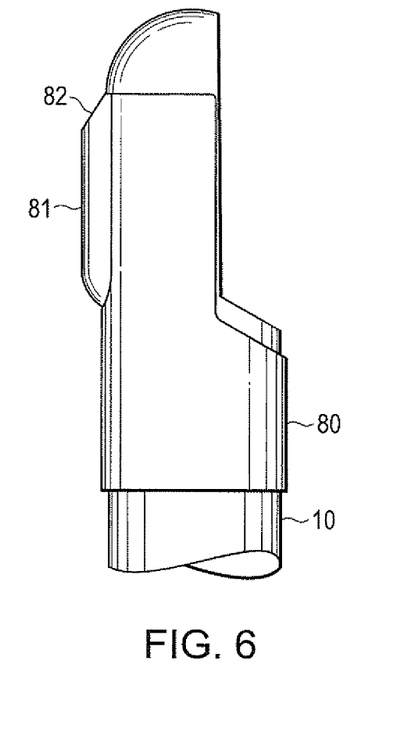
FIG. 6 is a perspective view of a distal tip of a surgical instrument in accordance with a second embodiment.
Figure 7:
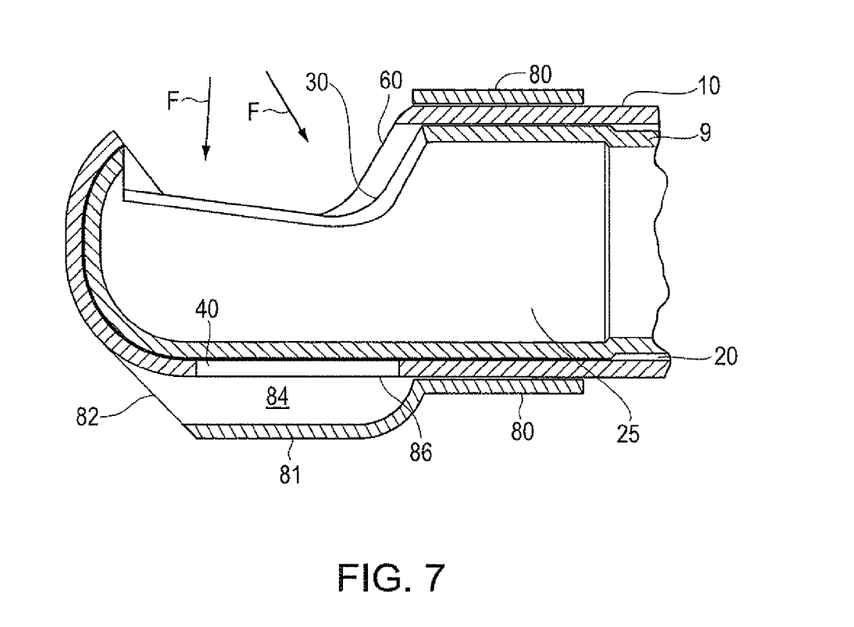
FIG. 7 is a side, cross-sectional view of the second embodiment showing the cutting windows being in complete alignment as occurs during a cutting operation.
Figure 8:
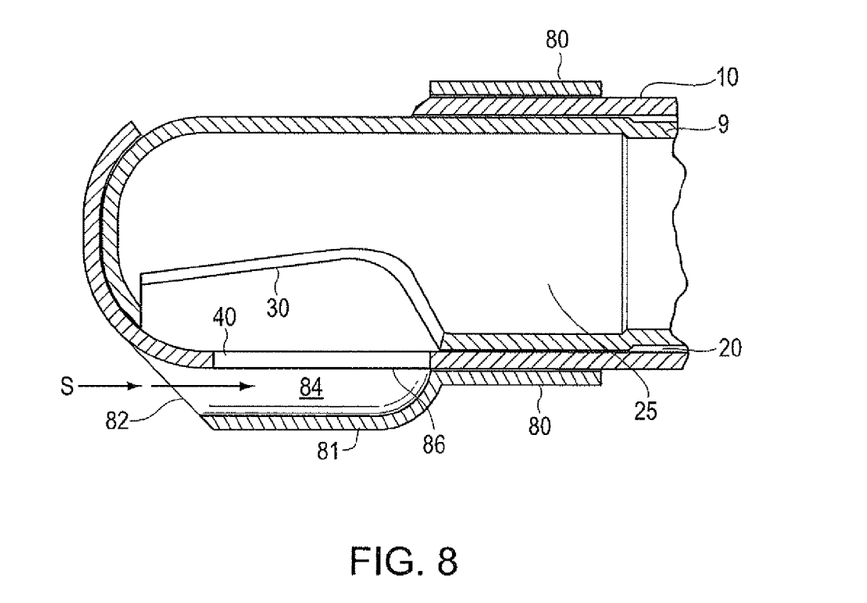
FIG. 8 is a side, cross-sectional view similar to FIG. 7, but with the cutting windows being in complete mis-alignment so that the surgical instrument can be used as a suction device.

FIGS. 6-8 show a second embodiment. The second embodiment provides a suction passage forming member in the form of a tube 80 that fits over the distal end of the outer cutting blade 10. The tube 80 includes a protruding portion 81 in which the passage of the suction passage forming member is disposed.

FIGS. 7 and 8 are views similar to FIGS. 4 and 5, but relate to the second embodiment using the tube 80. The protruding portion 81 includes an inlet 82, an internal suction passage 84 and an outlet 86 that communicates with the suction aperture 40. The second embodiment functions similar to the first embodiment, and thus its method of use will not be further described.

The tube 80 can be either permanently attached to the outer cutting blade 10 (for example, by welding), or it can be detachably attached to the outer cutting blade 10. For example, according to some embodiments, the tube 80 can slide onto and off of the outer cutting blade 10. The tube 80 can be plastic or metallic, and can be made from the same material as the outer cutting blade 10 or from a material that differs from the material used to make the outer cutting blade 10.

In both embodiments, it is preferable to make the inlet of the suction passage forming member (for example, inlet 52 or inlet 82) tapered to ease insertion of the surgical instrument into a passage of the patient. Both the first and second embodiments cause the overall diameter of the surgical instrument 8 to be increased. Thus, tapering the inlet (for example, 52 or 82) serves to ease insertion of the surgical instrument into a patient passage. Furthermore, it is preferable to make the half tube 50 and the tube 80 as small as possible to minimize the increase in the overall diameter of the surgical instrument. For example, according to one embodiment, the half tube 50 has a wall thickness of about 0.015 inches and a height of about 0.039 inches (i.e., a height equal to one-half of an outer diameter of 0.078 inches). However, these are just examples, and smaller (or larger) dimensions and wall thicknesses are possible. It is desirable that the half tube 50 or the tube 80 completely cover the suction aperture 40 and that the tapered front portion (having inlet 52/82) not allow any of the aperture 40 to be left exposed so as to prevent the unwanted cutting of tissue.

In the illustrated embodiments, the suction aperture 40 is disposed diametrically opposite from the cutting window 60 of the outer cutting blade 10. However, the suction aperture need not be precisely diametrically opposite from the cutting window 60.

When the instrument 8 is used for surgery, the surgical instrument 8 is inserted into a passage of a patient. Either before or after (or both before and after) a cutting operation is performed, the surgical instrument 8 can be used to perform a suctioning operation. The suctioning operation includes positioning the inner blade 9 relative to the outer blade 10 so that the cutting windows 30 and 60 are misaligned with each other so that the internal bore 25 of the cutting blade 9 does not communicate with the passage of the patient into which the surgical instrument is inserted through either of the cutting windows 30 and 60. A vacuum applied through the internal bore 25 of the cutting blade 9 draws material from the passage of the patient into the internal bore 25 through the inlets 52/82, the internal passage 54/84, the outlet 56/86 and the suction aperture 40. During performance of the suctioning operation, the inner cutting blade 9 is not rotated relative to the outer cutting blade 10.

Thus, it is unnecessary to withdraw the surgical cutting instrument 8 from the patient when switching between a cutting operation and a suctioning operation. Moreover, a separate suctioning wand may not be needed. Thus, the surgical procedure that is performed with the surgical instrument 8 can be performed more quickly and while causing less trauma to the patient.

In the illustrated embodiments, the inner and outer cutting blades 9 and 10 are straight. However, the surgical instrument 8 can have one or more bends in it such that it is not straight. In such an arrangement, the inner cutting blade 9 would be flexible. Flexible hollow cutting blades are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

The illustrated exemplary embodiments of the surgical tool as set forth above are intended to be illustrative and not limiting. Various changes may be made without departing from the spirit and scope of the invention.

What is claimed is:

1. A surgical instrument comprising:
a first cutting blade having a tubular body with a proximal end and a distal end, a cutting window disposed at a first side of the first cutting blade, a suction aperture disposed at a second side of the first cutting blade;
a second cutting blade having a tubular body with a proximal end and a distal end, a cutting window disposed at a side of the second cutting blade, the second cutting blade rotatably disposed inside of the first cutting blade such that the surgical instrument cuts tissue by rotating the second cutting blade within the first cutting blade while tissue is drawn into the cutting windows and severs the tissue by rotation of the second cutting blade; and
a suction passage forming member disposed over the suction aperture of the first cutting blade, the suction passage forming member including an inlet, an outlet and a passage between the inlet and the outlet, the outlet communicating with the suction aperture,
wherein the surgical instrument can be used as a suction tool by applying a vacuum through the internal bore of the second cutting blade while the second cutting blade is stopped from rotating with the cutting windows of the first and second cutting blades misaligned with each other so that the vacuum is applied through the suction aperture and the suction passage forming member.

2. The surgical instrument of claim 1, wherein the suction aperture is an elongated slot.

3. The surgical instrument of claim 1, wherein the suction passage forming member is half tube that is attached to an outer surface of the first cutting blade so as to cover the suction aperture, the half tube having a closed end and an open end, the open end defining the inlet.

4. The surgical instrument of claim 3, wherein the half tube is metallic.

5. The surgical instrument of claim 1, wherein the suction passage forming member is a tube that fits over at least part of the first cutting blade, the tube having a protruding portion in which the passage is disposed.

6. The surgical instrument of claim 5, wherein the tube is metallic.

7. The surgical instrument of claim 5, wherein the tube is plastic.

8. The surgical instrument of claim 5, wherein the tube is slidably detachable and attachable to the first cutting blade.

9. The surgical instrument of claim 1, wherein the suction passage forming member has a distal end at which the inlet is located, the distal end of the suction passage forming member being tapered.

10. The surgical instrument of claim 1, wherein the suction passage forming member is plastic.

11. The surgical instrument of claim 1, wherein the suction passage forming member is metallic.

12. The surgical instrument of claim 1, wherein the first and second cutting blades are made from a sterilizable material.

13. The surgical instrument of claim 1, wherein the first and second cutting blades are made from a metal.

14. The surgical instrument of claim 13, wherein the first and second cutting blades are made from stainless steel.

15. The surgical instrument of claim 1, wherein a passage exists between the first and second cutting blades through which a liquid can be supplied.

16. A surgical method comprising:
    inserting the surgical instrument of claim 1 into a passage of a patient; and
    performing a suctioning operation, the suctioning operation including:
    positioning the second cutting blade relative to the first cutting blade so that the cutting windows of the first and second cutting blades are misaligned with each other so that the internal bore of the second cutting blade does not communicate with the passage of the patient through either of the cutting windows of the first and second cutting blades, and
    applying a vacuum through the internal bore of the second cutting blade to draw material from the passage of the patient into the internal bore of the second cutting blade through the suction passage forming member and the suction aperture.

17. The surgical method of claim 16, wherein the first and second cutting blades are not rotated relative to each other during the step of applying the vacuum.

18. The surgical method of claim 16, further comprising:
    performing a cutting operation either before, after, or both before and after, performing the suctioning operation, wherein the cutting operation includes:
    rotating the second cutting blade relative to the first cutting blade while applying the vacuum through the internal bore of the second cutting blade.

19. The surgical method of claim 18, wherein the cutting operation further includes:
    supplying liquid through a passage that exists between the first and second cutting blades.

* * * * *